(12) United States Patent
Von Kaenel et al.

(10) Patent No.: US 10,492,930 B1
(45) Date of Patent: *Dec. 3, 2019

(54) STERILE WATER DISPERSION SYSTEM FOR ALLOGRAFT PREPARATION AND PROCESSING

(71) Applicant: Allosource, Centennial, CO (US)

(72) Inventors: Donald Von Kaenel, Westminster, CO (US); Daniel R. Hanten, II, Aurora, CO (US)

(73) Assignee: Allosource, Centennial, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/564,629

(22) Filed: Sep. 9, 2019

Related U.S. Application Data

(62) Division of application No. 15/259,376, filed on Sep. 8, 2016.

(60) Provisional application No. 62/256,438, filed on Nov. 17, 2015.

(51) Int. Cl.
*A61F 2/46* (2006.01)

(52) U.S. Cl.
CPC .... *A61F 2/4644* (2013.01); *A61F 2002/4646* (2013.01)

(58) Field of Classification Search
CPC ............... A61F 2/4644; A61F 2002/4646
See application file for complete search history.

(56) References Cited

U.S. PATENT DOCUMENTS

| | | | |
|---|---|---|---|
| 2009/0007601 A1 | 1/2009 | Suzuki et al. | |
| 2014/0312142 A1 | 10/2014 | Lovett | |
| 2016/0082483 A1* | 3/2016 | Zajdowicz | A61F 2/105 134/184 |
| 2016/0102425 A1 | 4/2016 | Scheckelhoff | |

* cited by examiner

*Primary Examiner* — Kevin Joyner
(74) *Attorney, Agent, or Firm* — James A. Sheridan; Sheridan Law, LLC

(57) ABSTRACT

There is disclosed a system and method for dispersing sterile water from a circulating high-purity water system to a processing field containing allograft tissue. One embodiment includes a fluid inlet that is fluidly coupled with and configured to receive sterile water from the water system. The dispersion system also includes at least first and second fluid outlets that are selectively operable to deliver respective first and second fluid streams into different areas of the processing field. At least one of the first and second fluid outlets may be associated with a regulator valve configured to provide an adjustable flowrate to conserve water pulled from the circulating water system to meet the needs of the application taking place within the processing field. Other embodiments are also disclosed.

7 Claims, 5 Drawing Sheets

STERILE WATER DISPERSION SYSTEM FOR ALLOGRAFT PREPARATION AND PROCESSING

REFERENCE TO PENDING PRIOR PATENT APPLICATION

This application is a divisional of U.S. patent application Ser. No. 15/259,376, filed Sep. 8, 2016 by Donald Von Kaenel, et al. for "STERILE WATER DISPERSION SYSTEM FOR ALLOGRAFT PREPARATION AND PROCESSING" which claims the benefit under 35 U.S.C. 119(e) of U.S. Provisional Patent Application No. 62/256,438, filed Nov. 17, 2015 by Donald Von Kaenel and Daniel R. Hanten II for "STERILE WATER DISPERSION SYSTEM FOR ALLOGRAFT PREPARATION AND PROCESSING," which patent application is hereby incorporated herein by reference.

BACKGROUND

An allograft includes bone, tendon, skin, or other types of tissue that is transplanted from one person to another. Allografts are used in a variety of medical treatments, such as knee replacements, bone grafts, spinal fusions, eye surgery, and skin grafts for the severely burned. Allografts come from voluntarily donated human tissue obtained from donor-derived, living-related, or living-unrelated donors and can help patients regain mobility, restore function, enjoy a better quality of life, and even save lives in the case of cardiovascular tissue or skin.

Allograft processing centers are generally responsible for processing and cataloging allografts collected by organ procurement organizations ("OPOs"). The OPOs are, in turn, responsible for collecting and/or recovering voluntarily donated tissues and gathering any pertinent medical information about those tissues before transferring them to the processing center.

Once an allograft is received, the allograft processing center is then responsible for processing the allograft and readying it for safe and effective medical use. Such processing may involve several steps including inspection, testing, cleansing, and cataloging, all performed in government-certified (or equivalent) laboratories and subject to strict standards and regulations. To render the risk of disease transmission extremely remote, allograft tissue is processed to eliminate risk of infection transmission and tissue rejection. Grafts are sterilized and tissues are carefully preserved in an effort to retain the original structural and biological integrity of the graft. Quality assurance checks are incorporated into the preparation process, including aerobic and anaerobic cultures and any applicable additional testing.

Careful steps must be taken to ensure sterile integrity throughout the preparation process discussed above. In this regard, an allograft processing center often utilizes a high-purity water system that circulates sterile water throughout the processing center to each of the laboratories (e.g., clean rooms) used in the preparation process. Using this type of "loop" circulation system, sterile water that meets defined microbial limits is typically delivered via a distribution line to the processing field. Water is then returned as feed to the distillation and/or filtration system via a feedback loop for sterilization and reentry into the distribution line.

Loop water systems are effective at transporting water to the sterile environment, but they are expensive to operate. Every gallon of sterile injection water consumed comes at a cost, and, therefore, exercising control over water dispersal is paramount.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

One embodiment provides a system for dispersing sterile water from a circulating high-purity water system into a processing field containing allograft tissue. The system may include a fluid inlet that is fluidly coupled with and configured to receive sterile water from the water system. The system may also include at least first and second fluid outlets, wherein the first and the second fluid outlets are selectively operable to deliver respective first and second fluid streams to the processing field, and at least one of the first and the second fluid outlets is configured to deliver fluid into the processing field at an adjustable flow rate.

Another embodiment provides a method of dispersing sterile water from a circulating high-purity water system to a processing field containing allograft tissue using a dispersal system having a fluid inlet fluidly coupled with the water system and at least first and second selectively-operable fluid outlets. The method may include activating the first fluid outlet to deliver a first fluid stream to a first area of the processing field, wherein the first fluid stream comprises an unimpeded fall of the sterile water into the first area of the processing field. The method may also include adjusting a flow rate of the first fluid stream to achieve a desired flow rate of the first fluid stream exiting the first fluid outlet, and activating the second fluid outlet to deliver a second fluid stream to a second area of the processing field.

Yet another embodiment provides a water dispersion system for dispersing sterile water from a loop water system into an allograft processing field. The water dispersion system may include (1) a fluid inlet configured to receive the sterile water from the loop water system; (2) a first fluid outlet configured to disperse a first fluid stream of the sterile water into a first area of the allograft processing field; and (3) a second fluid outlet configured to disperse a second fluid stream of the sterile water into a second area of the allograft processing field. The first fluid outlet and the second fluid outlet are offset from the allograft processing field, and the first fluid stream may remain at all times fluidly separate from the second fluid stream.

Other embodiments are also disclosed.

Additional objects, advantages and novel features of the technology will be set forth in part in the description which follows, and in part will become more apparent to those skilled in the art upon examination of the following, or may be learned from practice of the technology.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which.

DETAILED DESCRIPTION

Figure 1:
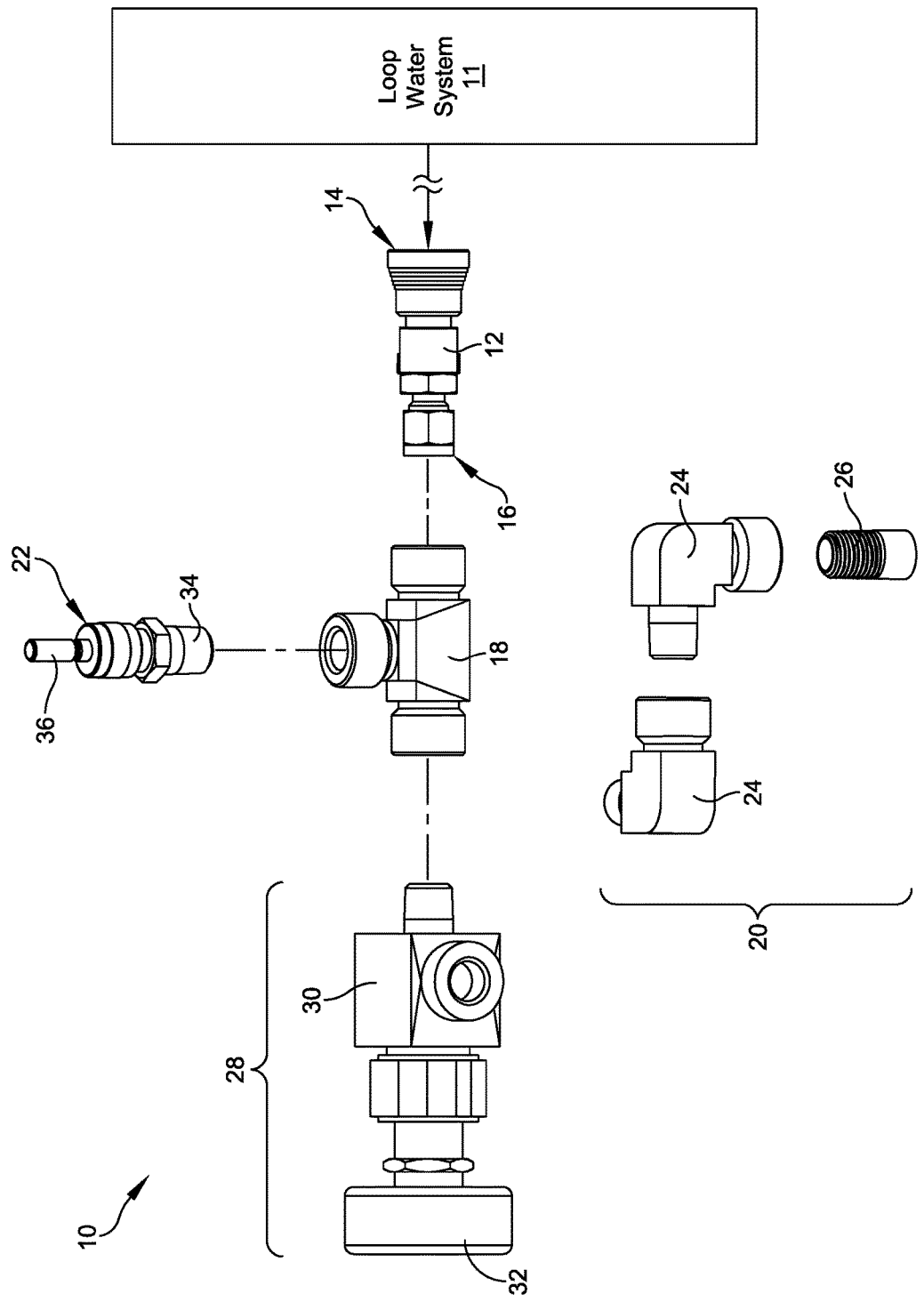
FIG. 1 illustrates an exploded view of one embodiment of a water dispersion system for dispersing sterile water from a loop water system into an allograft processing field in a variable and controlled manner.

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

Current mechanisms for dispersing water from a loop water system into the processing field where allograft tissue preparation occurs (e.g., into a beaker containing allograft tissue or in connection with other vessels and/or equipment containing or being exposed to allograft tissue) do not allow processing personnel to disperse sterile water in a variety of controlled ways to aid in the thawing, cleaning, purging, and/or rinsing of donated tissue. For instance, current dispersion mechanisms provide for a singular flow stream having a set flow rate. A singular flow stream results in lost efficiency due to the fact that technicians cannot multi-task while availing themselves of a single flow stream. A set flow rate leads to wasted water via unnecessarily high flow rates for certain applications. Further, current sterile-water dispersion approaches generally allow water delivery equipment to come into close proximity or contact with the processing field, which risks the backflow of microbes into the loop water system and puts the sterile integrity of the allograft processing center at risk.

Various embodiments of the systems and methods described herein relate to controlling the dispersion of sterile water from a circulating or loop high-purity water distribution system (hereinafter a "loop water system" or "loop") to a processing field containing human allograft tissue in a manner that protects the loop water system from microbial compromise. One embodiment provides a dispersion system that includes at least two fluid outlets that may direct sterile water to different areas within the processing field. Because a variety of activities take place within the processing field (e.g., the thawing, cleaning, purging, and/or rinsing of donated tissue), multiple fluid outlets allow a technician to multitask by directing one fluid stream to a first area within the processing field and another fluid stream to another area within the processing field. For example, a tissue sample may be arranged for continuous thawing beneath a first fluid stream, while the technician may take advantage of the second fluid stream to simultaneously perform an array of alternate tasks. In addition, at least one of the dispersion system's fluid outlets may be adjustable, thereby allowing the technician to control the water flow to achieve a desired flow rate, conserving up to hundreds of gallons of costly sterile water during a single processing session. Moreover, both fluid outlets may be configured to prevent microbial wicking or travel from the processing field back into the loop water system, ensuring the sterile integrity of the processing center's water as a whole.

Figure 2:
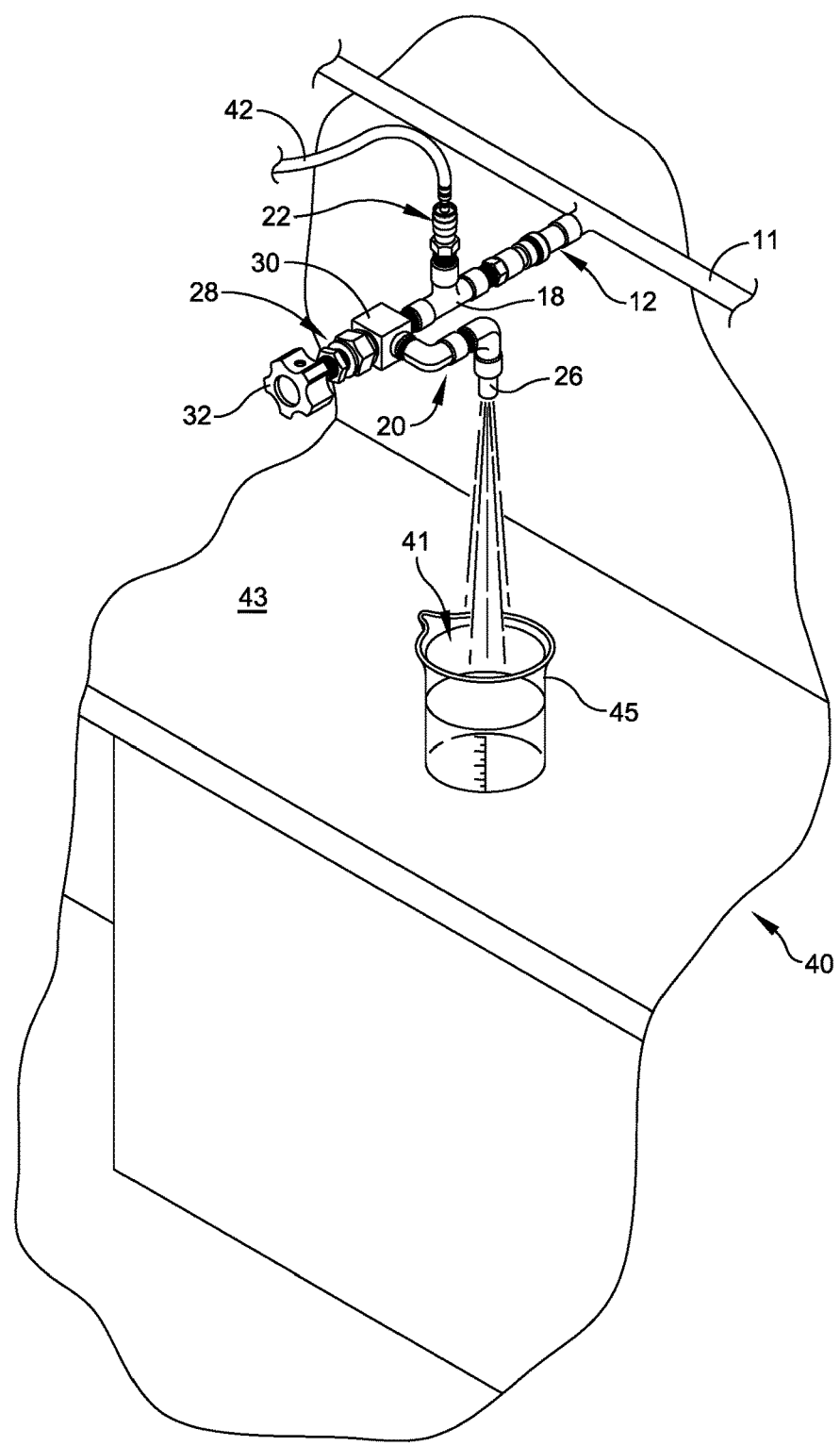
FIG. 2 illustrates a perspective view of the water dispersion system of FIG. 1, as installed above a processing field.

FIGS. 1-2 illustrate respective exploded and perspective views of one embodiment of a water dispersion system 10 for dispersing sterile water from a loop water system 11 into a processing field in a variable and controlled manner. In this embodiment, water dispersion system 10 may include an inlet 12, which fluidly couples with and receives sterile water from loop water system 11. Embodiments of inlet 12 may be formed of stainless steel and may take any appropriate size, shape, and/or configuration capable of fluidly coupling with loop water system 11. In one embodiment, inlet 12 may be a commercially available quick-connect body such as, for example, Swagelok Part No. SS-QC4-B-4PM.

Figure 3:
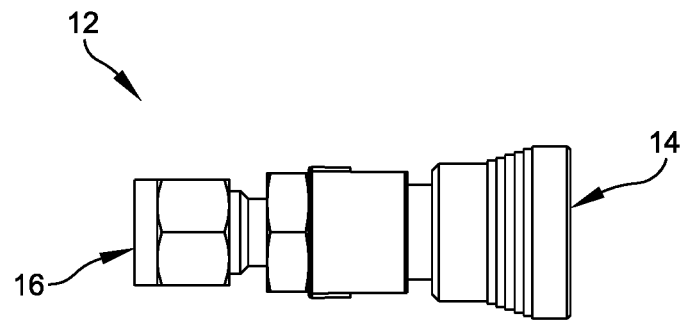
FIG. 3 illustrates a side view of one embodiment of a fluid inlet of the water dispersion system of FIGS. 1-2.

FIG. 3 illustrates a side view of one embodiment of inlet 12. In this embodiment, and as detailed in FIG. 1, inlet 12 may have a first end 14 that directly connects to loop water system 11 and a second end 16 that forms a male coupler configured to attach to a tee fitting 18. Tee fitting 18 may be a tee-shaped stainless steel pipe fitting configured to route sterile water between a first fluid outlet 20 and a second fluid outlet 22. In one embodiment, tee fitting 18 may be a commercially available fitting such as, for instance, Swagelok Part No. SS-4-T.

Figure 4:
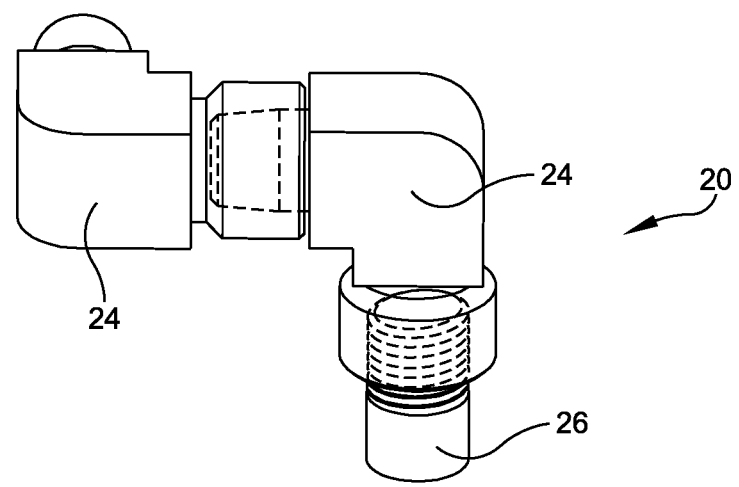
FIG. 4 illustrates a perspective view of one embodiment of a first fluid outlet of the water dispersion system of FIGS. 1-2.

FIG. 4 illustrates a side view of one embodiment of first fluid outlet 20. In this embodiment, and as detailed in FIGS. 1 and 4, first fluid outlet 20 may be a subassembly formed of serialized right-angle fittings 24 (e.g., Swagelok Part No. SS-4-SE) and a single-threaded-end pipe nipple 26 (e.g., McMaster-Carr Part No. 9110T11). As shown in FIG. 2, when water dispersion system 10 is connected to loop water system 11, pipe nipple 26 may be directed downward such that sterile water flowing from first outlet 20 cascades unimpeded in a downward direction in a waterfall-like manner into a first area 41 of a processing field 40. This type of free flow allows only water, rather than a hose or other water-delivery device, to come into contact with processing field 40, thereby preventing backflow, travel, and/or wicking of microbes upward from processing field 40 and back into loop water system 11. For example, water may be directed from first fluid outlet 20 into a beaker or other vessel 45 containing allograft material without risking contamination of the loop's sterile water supply as a result of microbial backflow from vessel 45, through the delivery hose, and upward into loop water system 11.

Figure 5:
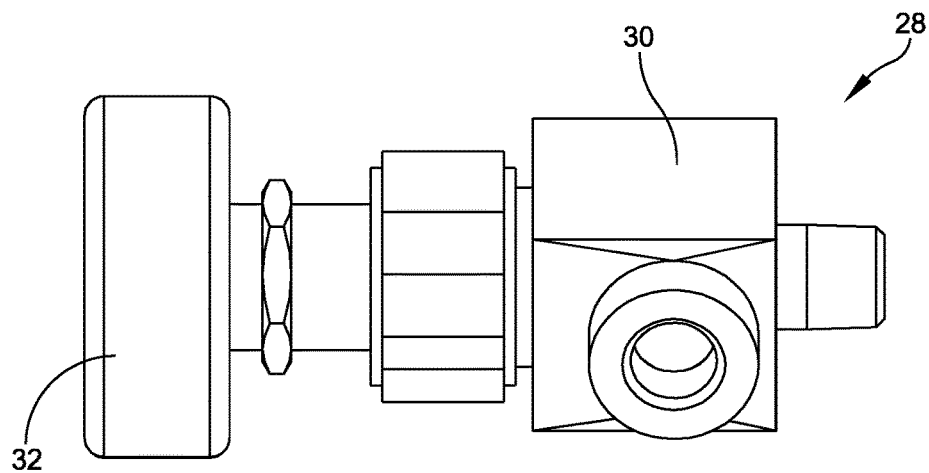
FIG. 5 illustrates a perspective view of one embodiment of a regulator valve and flow rate-adjustment handle associated with the first fluid outlet of FIG. 4.

To allow for maximum user control over the sterile water flowing from first fluid outlet 20, a regulator valve 28, detailed in FIGS. 1 and 5, may be connected between tee fitting 18 and first fluid outlet 20. Regulator valve 28 may be any appropriate valve having a size, shape, type, and/or configuration designed to allow for manual adjustment of a flow rate of sterile water through first fluid outlet 20. In one embodiment, regulator valve 28 may be a subassembly formed of a high-purity, high-pressure angle-pattern valve 30 (e.g., Swagelok Part No. SS-DSM4F4A) equipped with an anodized rotating handle 32. Regulator valve 28 may allow for a wide range of flow rates, depending upon the application occurring in the processing field. For example, at 100%, 75%, 50%, and 25% open, regulator valve 28 may provide respective flow rates of 504 liters/hour, 396 liters/hour, 252 liters/hour, and 126 liters/hour. This ability to adjust the flow rate gives the technician maximum flexibility in controlling the amount of water used and in limiting water use to only that needed for a particular application, thereby significantly reducing the amount of sterile water pulled from the loop water system.

Figure 6:
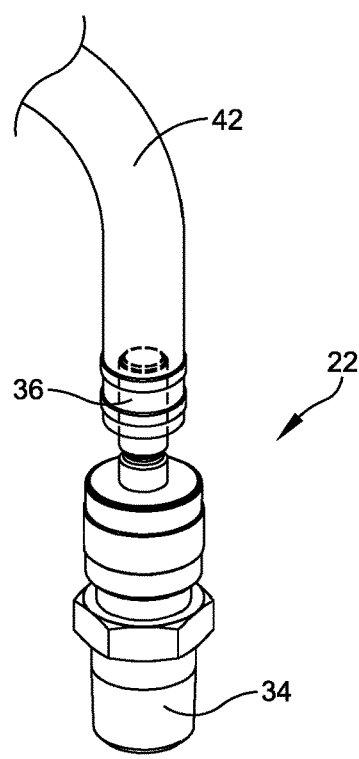
FIG. 6 illustrates a perspective view of one embodiment of a second fluid outlet of the water dispersion system of FIGS. 1-2.

Returning to FIG. 1, beyond directing water to first fluid outlet 20, tee fitting 18 may also direct water to second fluid outlet 22, giving technicians a second usable water outlet that allows for multitasking within the same processing field 40. In one embodiment detailed in FIGS. 1 and 6, second fluid outlet 22 may be formed of a quick-connect stem (e.g., Swagelok Part No. SS-QC4-S-4PM) having a first end 34 that forms a male coupler configured to connect with tee fitting 18 and a second end 36 configured to connect with a delivery hose 42. The delivery hose may be directed to a second area 43 within processing field 40 (FIG. 2) than the flow from first fluid outlet 20, depending on the current application, task, and/or needs of the technician. Further, flow and/or pooling of fluid from second fluid outlet 22 may be kept entirely fluidly separate from the flow and/or pooling of fluid from first fluid outlet 20, preventing crossover between the two streams.

To prevent contamination or microbial wicking through hose 42 connected to second fluid outlet 22, the hose may be suspended—either manually, by using a fixture, or by allowing the hose to hang freely—such that hose 42 does not come into contact with water or the surfaces of tools and/or equipment that have been exposed to microbes of the allograft material being processed within processing field 40. In one embodiment, the "open" hose 42 connected with second fluid outlet 22 (i.e., hose 42 without a pressure tip) may provide a flow rate of 456 liters/hour.

This second fluid outlet 22 provides technicians with maximum flexibility in accomplishing varying tasks within a single processing field. For example, a technician may perform a continuous thawing of frozen allograft tissue in conjunction with first fluid outlet 20, while simultaneously performing an array of tasks associated with processing the human tissue and requisite equipment (e.g., cleaning, purging, rinsing, etc.) in conjunction with second fluid outlet 22. In performing this variety of simultaneous tasks, the technician need not stop to change nozzle tips, as the technician has flow-rate adjustable access to both free flowing water from first fluid outlet 20 and the constrained flow from hose 42, which is coupled with second fluid outlet 22.

While tee fitting 18 is described as a pipe fitting, some embodiments may incorporate a tee-valve that offers further regulation of flow across first fluid outlet 20 and/or second fluid outlet 22, providing maximum control over the dispersion of water from the loop.

Embodiments of water dispersion system 10 may also incorporate a backflow device (not shown). This device may have any appropriate size, shape, type and/or configuration to further inhibit microbial backflow.

Using water dispersion system 10, allograft preparation technicians may employ a preparation process that utilizes at least two water streams and adjusts the flow of those streams to achieve maximum control, both over where water is directed into the processing field and over how much water is directed into the processing field to meet the needs of the tasks at hand. All of this may be accomplished without risking contamination to the loop water system.

Figure 7:
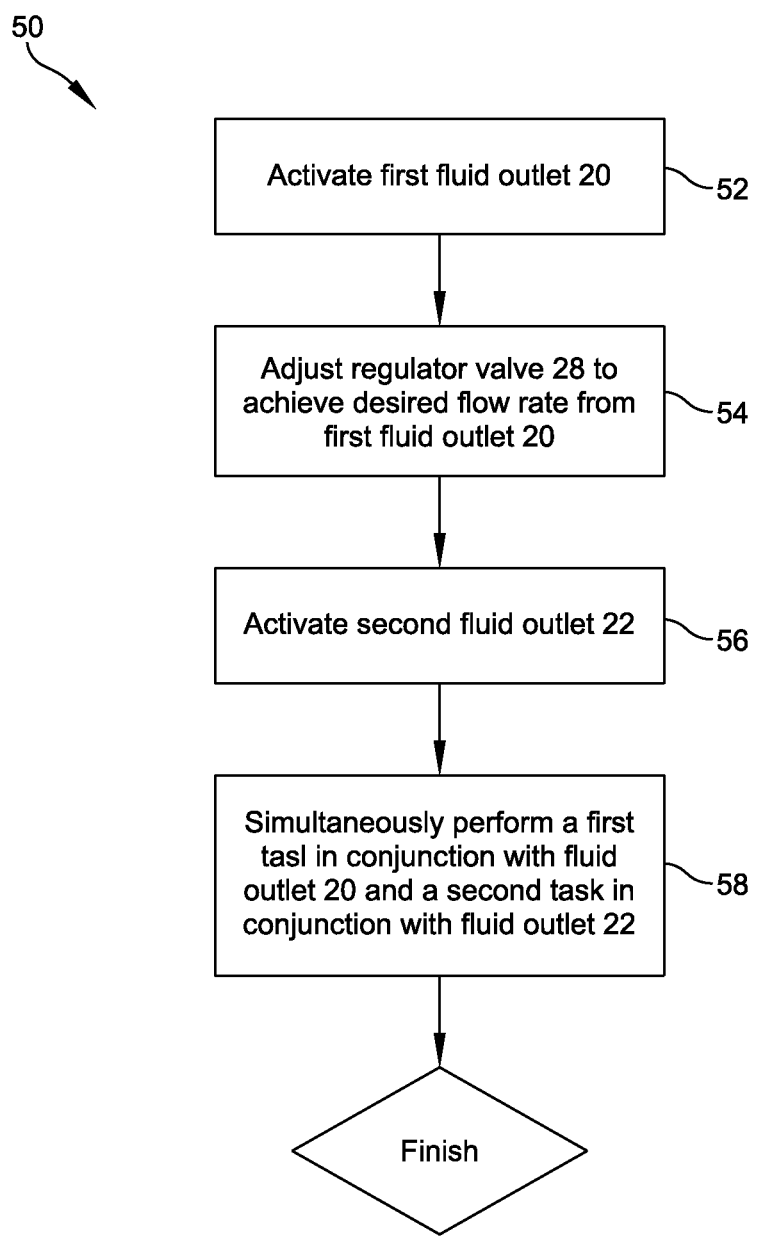
FIG. 7 provides a flowchart depicting an exemplary method of dispersing sterile water from a circulating high-purity water system using the water dispersion system of FIGS. 1-2.

FIG. 7 depicts a flowchart detailing an exemplary method 50 of dispersing sterile water from a circulating high-purity water system. Method 50 may initiate with activating first fluid outlet 20 to deliver a first sterile fluid stream to a first area 41 of processing field 40 (52). The method may continue with adjusting regulator valve 28 (54) to regulate a flow rate of the first fluid stream such that a desired flow rate exits first fluid outlet 20. The desired flow rate may be a function of the task(s) to be performed in conjunction with the first sterile fluid stream. Method 50 may also include activating second fluid outlet 22 (56) to deliver a second fluid stream to a second area 43 of processing field 40. With both first and second fluid outlets activated, the technician may simultaneously perform (58) a first task in first area 41 of processing field 40 and a second task in second area 43 of processing field 40.

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. A method of dispersing sterile water from a circulating high-purity water system to a processing field containing allograft tissue using a dispersal system having a fluid inlet fluidly coupled with the water system and at least first and second selectively-operable fluid outlets, comprising:
   activating the first fluid outlet to deliver a first fluid stream to a first area of the processing field, wherein the first fluid stream comprises an unimpeded fall of the sterile water into the first area of the processing field;
   adjusting a flow rate of the first fluid stream to achieve a desired flow rate of the first fluid stream exiting the first fluid outlet; and
   activating the second fluid outlet to deliver a second fluid stream to a second area of the processing field.

2. The method of claim 1, wherein the first area of the processing field comprises a vessel containing allograft tissue.

3. The method of claim 1, wherein the second fluid outlet comprises a quick-connect stem adapted to attach to a fluid-delivery hose directed toward the second area of the processing field.

4. The method of claim 3, wherein the second area of the processing field is fluidly separate from the first area of the processing field.

5. The method of claim 3, wherein the first fluid stream is at all times fluidly separate from the second fluid stream.

6. The method of claim 1, further comprising adjusting a flow rate of the second fluid stream to achieve a desired flow rate of the second fluid stream exiting the second fluid outlet.

7. The method of claim 1, further comprising simultaneously performing a first task within the first area of the processing field and in conjunction with the first fluid stream and a second task within the second area of the processing field and in conjunction with the second fluid stream.

\* \* \* \* \*